(12) United States Patent
Okubo et al.

(10) Patent No.: US 6,780,983 B2
(45) Date of Patent: Aug. 24, 2004

(54) POLYPEPTIDE HAVING WATER CHANNEL ACTIVITY AND DNA SEQUENCE

(75) Inventors: Kousaku Okubo, Mino (JP); Hiroshi Kuriyama, Toyonaka (JP); Shiro Mita, Ashiya (JP); Naruhiro Ishida, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 408 days.

(21) Appl. No.: 09/849,980

(22) Filed: May 8, 2001

(65) Prior Publication Data

US 2002/0123611 A1 Sep. 5, 2002

Related U.S. Application Data

(62) Division of application No. 09/381,810, filed as application No. PCT/JP98/01371 on Mar. 27, 1998, now Pat. No. 6,252,046.

(30) Foreign Application Priority Data

Mar. 28, 1997 (JP) ............................................. 9-094845

(51) Int. Cl.⁷ ............................................. C07H 21/02
(52) U.S. Cl. ........................ 536/23.1; 536/23.1; 435/6; 435/69.1; 530/350
(58) Field of Search .............................. 536/23.1; 435/6, 435/69.1; 530/350

(56) References Cited

PUBLICATIONS

Ishibashi et al., Genomics, vol. 27, pp. 352–354, 1995.*
Thomas Walz et al., "Biologically Active Two–Dimensional Crystals of Aquaporin Chip", The Journal of Biological Chemistry, 1994, vol. 269, No. 3, pp. 1583–1586.
Mark L. Zeidel et al., "Ultrastructure, Pharmacologic Inhibition, and Transport Selectivity of Aquaporin Channel–Forming Integral Protein in Proteoliposomes", Biochemistry, 1994, vol. 33, pp. 1606–1615.

* cited by examiner

Primary Examiner—Karen Cochrane Carlson
Assistant Examiner—Hope A. Robinson
(74) Attorney, Agent, or Firm—Connolly Bove Lodge & Hutz LLP

(57) ABSTRACT

The present invention has its objects to provide a novel polypeptide having water channel activity and to a DNA sequence encoding for the polypeptide.

This invention is related to a novel polypeptide having water channel activity which has the amino acid sequence, within the molecule thereof, shown in the sequence listing under SEQ ID NO: 1.

2 Claims, No Drawings

US 6,780,983 B2

POLYPEPTIDE HAVING WATER CHANNEL ACTIVITY AND DNA SEQUENCE

CROSS-REFERENCE TO RELATED APPLICATION

This application is a divisional of U.S. patent application Ser. No. 09/381,810 filed Oct. 19, 1999, now U.S. Pat. No. 6,252,046, which is the national phase of PCT/JP98/01371 filed Mar. 27, 1998 and claiming priority from Japanese Hei-9-094845 filed Mar. 28, 1997.

TECHNICAL FIELD

The present invention relates to a novel, human adipose tissue-derived polypeptide having water channel activity and to a DNA sequence encoding for the polypeptide.

BACKGROUND ART

The permeation of water through a cell membrane generally occurs slowly by way of diffusion into the lipid bilayer which is the main structure of the cell membrane. Recently, however, it was discovered that, in certain kinds of cells, water is transferred rapidly through the cell membrane, suggesting the involvement in the above phenomenon of some membrane protein selectively permeable to water. Thereafter, such membrane proteins of various kinds have actually been isolated. Such membrane proteins are designated as water channels. In this specification, the function of the above water channels which has selective permeation of water through the cell membrane is referred to as "water channel activity". The water channels may be permeable to water alone or permeable to not only water but also low-molecular-weight substances such as glycerol and urea.

As a membrane protein having such water channel activity, there have been isolated a group of membrane proteins known as aquapolins (AQPs). Furthermore, some aquapolin genes have so far been cloned, and aquapolins such as AQP1 through AQP5, FA-CHIP and AQP-γTIP have been discovered in mammals, amphibians, plants, etc. [cf. e.g. Akira Sasaki, Igaku no Ayumi (Advances in Medicine), vol. 173, No. 9, 1995].

P. Agre et al. reported, in Science (vol. 256, pp. 385 to 387, 1992) that Xenopus laevis oocytes in which the in vitro transcript RNA for CHIP28, the current designation of which is AQP1, had been introduced showed increased water permeability. In Science (vol. 264, pp. 92 to 95, 1994), B. A. van Oost et al. disclosed the amino acid sequence of human AQP2 and suggested that this should be involved in vasopressin-dependent urine concentration.

In Proc. Natl. Acad. Sci. USA (vol. 91, pp. 6269 to 6273, 1994), Ishibashi et al. disclosed the nucleotide sequence of the gene for renal collecting tubule-derived AQP3 and the amino acid sequence encoded thereof. Ishibashi et al. confirmed its water channel activity by injecting the AQP3 cRNA into Xenopus laevis oocytes and measuring the water permeability thereof. Ishibashi et al. reported that this AQP3 transported not only water but also nonionic small molecules such as urea and glycerol.

In Proc. Natl. Acad. Sci. USA (vol. 91, pp. 13052 to 13056, 1994), J. S. Jung et al. reported about the isolation of AQP4. This AQP4 is known to occur most abundantly in mammalian brains and have mercury resistance. In J. Biol. Chem. (vol. 270, pp. 1908 to 1912, 1995), S. Raina et al. who prepared rat salivary gland-derived AQP5 cDNA describe the nucleotide sequence of the cDNA and the amino acid sequence encoded thereby. S. Raina et al. cloned the cDNA by utilizing the occurrence of an NPA sequence and confirmed its function by observing that the cRNA enhances the water permeability of Xenopus laevis oocytes.

The aquapolin family mentioned above is considered to be involved in water metabolism in mammals and, for example, it has been confirmed that AQP2 is found only in the renal collecting tubule luminal membrane, which is indicative of its close association with the vasopressin-urea concentration system, and its involvement in renal diseases has become acknowledged. Therefore, such membrane proteins having water channel activity are of importance in any attempt to develop novel therapies for water-associated diseases.

Meanwhile, the expression of the aquapolin family mentioned above has been confirmed in such organs as kidney, brain, gall bladder, eye, intestine, salivary gland and bronchus but there is no report as yet about the occurrence of membrane proteins having water channel activity in other organs or tissues, particularly in adipose tissue.

SUMMARY OF THE INVENTION

In view of the above-mentioned state of the art, the present invention has for its object to provide a novel membrane protein having water channel activity and a DNA sequence encoding for the polypeptide.

The present invention is related to a novel polypeptide having water channel activity which has the amino acid sequence, within the molecule thereof, shown in the sequence listing under SEQ ID NO:1.

The present invention is also related to a nucleotide sequence itself which codes for a polypeptide having, within the molecule thereof, the amino acid sequence shown in the sequence listing under SEQ ID NO:1 and having water channel activity.

The present invention is further related to the DNA sequence shown in the sequence listing under SEQ ID NO:2.

The present invention is still further related to a polypeptide having water channel activity which has the amino acid sequence, within the molecule thereof, encoded by the nucleotide No. 173 to No. 1198 of the nucleotide sequence shown in the sequence listing under SEQ ID NO:2.

DETAILED DESCRIPTION OF THE INVENTION

In the following, the present invention is described in detail.

The polypeptide of the present invention has the amino acid sequence shown in the sequence listing under SEQ ID NO:1. This polypeptide has a sequence composed of three amino acids, namely asparagine-proline-alanine, as the amino acid Nos. 195 to 197. However, the characteristic feature common to the so-far known AQPs, that said asparagine-proline-alanine sequence occurs twice, is not found in the polypeptide of the present invention. That this polypeptide has water channel activity can be confirmed from the fact that it enhances the water permeability of Xenopus laevis oocytes.

The above polypeptide may be generated by translation by a protein synthesis system constituted, in vivo or in vitro, based on the nucleotide sequence coding for the amino acid sequence of said polypeptide. The nucleotide sequence of the present invention substantially has a region coding for the amino acid sequence of said polypeptide and, where necessary, may contain one or more other regions such as a promoter region. In the protein synthesis based on genetic information, the information carried by the gene DNA is transcribed into mRNA as the result of DNA-dependent RNA synthesis aided by RNA polymerase. And, this mRNA is translated into the amino acid sequence in a tRNA-containing protein synthesis system. Therefore, the nucleotide sequence of the present invention includes not only the DNA sequence but also the RNA sequence. Furthermore, since it is generally known that, for an amino acid, there is one or a plurality of codons corresponding thereto, it is a matter of course that the above-mentioned nucleotide sequence is not limited to only one sequence but may include nucleotide sequences resulting from substitution of another synomyous codon coding for the same amino acid.

The above polypeptide can be formed based on the genetic information carried by the DNA sequence shown in the sequence listing under SEQ ID NO:2. This polypeptide is encoded by that portion of the nucleotide sequence shown in the sequence listing under SEQ ID NO:2 which ranges from the nucleotide No. 173 to No. 1198. Of the DNA sequence shown in the sequence listing under SEQ ID NO:2, the nucleotide sequences other than the portion of said nucleotide numbers are noncoding regions, among which the polyadenylation consensus sequence AATAAA occurs at the nucleotide No. 1234 to No. 1239. Other possible reading frames of said DNA sequence shown under SEQ ID NO:2 can be excluded from consideration, since the polypeptides encoded are very small-sized, hence considered to be incapable of performing any water channel function.

It has been confirmed by the inventors that the full-length sequence of the above nucleic acid bases has no counterpart sequence either in GenBank or in dbEST.

The polypeptide of the present invention has water channel activity in adipose tissue. While adipose tissue is distributed in various parts of the living organism, the polypeptide of the present invention has an action to control the transfer of water in such adipose tissue and is expected to be effective in upholding normal functions of adipose tissue at various sites.

BEST MODES FOR CARRYING OUT THE INVENTION

The above-mentioned DNA sequence given under SEQ ID NO:2 corresponds to the nucleotide sequence of cDNA obtained from human adipose tissue by cloning. Human adipose tissue is a tissue which stores fat as energy reserves. It is known that various proteins are formed in this adipose tissue. A 3'-directed DNA library is known as a cDNA library from which the genes actually expressed in this adipose tissue or, in other words, the mRNA composition in this adipose tissue can be copied faithfully. This 3'-directed DNA library contains only those specified 3'-terminal regions of mRNAs which range from poly(A) to the MboI site which is a restriction enzyme recognition site upstream of said poly(A) and, therefore, said library is suited for template preparation by the PCR technique. Therefore, by extracting a clone from this library and using it to determine a longer nucleotide sequence including the amino acid coding region from this complete adipose tissue cDNA library, it becomes possible to obtain the genetic information concerning the protein which is actually formed in adipose tissue. The DNA sequence of the present invention as shown under the above-mentioned SEQ. ID. NO:2 is found by such cloning. A method of obtaining the cDNA by cloning from human adipose tissue is now describe in detailed.

Known as said method is, for example, the method described in Biochem. Biophys. Res. Commun., 221, 286 to 289 (1996). According to this method, the total RNA is first separated from adipose tissue and, when necessary, purified to give poly(A) RNA. For this purification, commercially available purification kits can be used. For example, Pharmacia's Quick prep mRNA purification kit or the like in which oligo(dT)-cellulose and various buffers are used in combination can judiciously be employed. Then, a double-stranded cDNA is synthesized using a pUC19 system vector primer and the double-stranded cDNA so synthesized is selectively cleaved with the restriction enzyme MboI (which recognizes the nucleotide sequence GATC). On that occasion, the GATC sequence on the vector molecule side, which can be methylated to give $G^m$ATC when replication is effected in dam$^+$ bacterial cells, is not cleaved with MboI. As the cleaved cDNA is subjected to self-cyclization using E. coli ligase, a plasmid containing a cDNA fragment extending from poly(A) to the nearest MboI site is completed. This plasmid is introduced into Escherichia coli, followed by cultivation and selection of a transformant E. coli colony. Then, the cDNA in said colony is amplified by the PCR technique using appropriate PCR primers.

On the other hand, the full-length double-stranded cDNA synthesized using the pUC19 system vector primer is cleaved at the 5' end using T4 polymerase and subjected to cyclization using T4 ligase and introduction into Escherichia coli for transformation. From among the thus-obtained transformant colonies, the desired colony is obtained by screening using, as a probe, a labeled form of the adipose tissue-specific cDNA obtained from said 3'-directed DNA library by the method mentioned above. The insert cDNA in this colony is amplified by the PCR technique using appropriate PCR primers. The amplification product is purified and, after sonication, subcloned into the M13 phage.

The nucleotide sequence of the thus-cloned cDNA can be determined, for example, by reaction with a primer dye, purification and analysis using an automated sequencer or the like. In this manner, the DNA sequence of the present invention can be obtained.

The polypeptide of the present invention has water channel activity. This water channel activity can be confirmed by observing an enhancement of water permeability in Xenopus laevis oocytes. It is known that no AQP family gene has been expressed in Xenopus laevis oocytes and, therefore, any increase in water permeability as caused by the injected mRNA can be easily confirmed. For this reason, said oocytes are widely used in confirming water channel activity. For example, in Proc. Natl. Acad. Sci. USA, vol. 91, pp. 6269 to 6273 (1994), Ishibashi et al. confirmed the water channel activity by inserting the AQP3 cDNA into the pSP64T-derived BlueScript vector, synthesizing the cRNA using T7 RNA polymerase, injecting this cRNA into Xenopus laevis oocytes and, after 48 to 62 hours of incubation following injection, observing an increase in water permeability and in the volume of the oocyte.

The polypeptide encoded by the DNA sequence of the present invention can be identified by analyzing the amino acid sequence of the polypeptide synthesized in an Escherichia coli protein synthesis system constituted in vitro. In this case, the methods of identifying N- and C-terminal sequences of expression products as described in Shin Seikagaku Jikken Koza (Experiments in Biochemistry, A New Course) 1 (published by Tokyo Kagaku Dojin), pages 22 to 24 can be employed.

The following examples illustrate the present invention in further detail. These examples are, however, by no means limitative of the scope of the present invention.

EXAMPLE 1

Determination of DNA Nucleotide Sequence

According to a recent report [Biochem. Biophys. Res. Commun., 221, 286 to 289 (1996)], a DNA for an adipose tissue-specific collagen-like factor has been cloned using a 3'-directed DNA library containing only those specified 3'-terminal regions of RNA molecules which range from poly(A) to the restriction enzyme MboI site upstream thereof [Nature Genet., 2, 173 to 179 (1992)], which library makes it possible not only to identify the gene under expression but also to examine the frequency of expression or amount of expression. In accordance with the method described in the above report, the DNA nucleotide sequence of the present invention was determined using an adipose tissue-specific 3'-directed DNA library.

Method

Reverse transcriptase was added to poly(A)+ RNA separated and purified from human adipose tissue using a Quick prep mRNA purification kit, followed by insertion into λ ZAP II containing the pUC19 system vector pBluescript and introduction into *Escherichia coli*. Screening carried out using an adipose tissue-specific partial DNA as a probe gave a colony of transformant *Escherichia coli*. Then, together with two primers (SK: 5'CGCTCTAGAACTAGTGGATC3'; T7: 5'GTAATACGACTCACTATAGGGC3'), PCR [polymerase chain reaction; (30 seconds at 95° C.+30 seconds at 50° C.+60 seconds at 70° C.)×15 cycles, followed by (30 seconds at 95° C.+60 seconds at 70° C.)×15 cycles], was carried out and, after sonication, the product was subcloned in M13. A primer dye was added thereto and, after purification, the nucleotide sequence of the DNA was analyzed using an automated sequencer. The nucleotide sequence obtained is shown in the sequence listing under SEQ ID NO:2.

EXAMPLE 2

Examination as to Water Permeability

As for the studies on the water permeability of the AQP family, there are reports about AQP1 [Science, 256, 385–387 (1992)] and AQP3 [Proc. Natl. Acad. Sci. USA, 91, 6269–6273 (1994)] in which RNA was introduced into *Xenopus laevis* oocytes, in which AQP family genes have not been expressed, and then the water permeability was calculated from changes in the surface area and volume of said oocytes in a hypotonic culture medium. Therefore, the membrane protein encoded by the DNA of the present invention was checked for water permeability according to the method described in the references cited above.

Test Method

The RNA (10 ng) obtained in Example 1 from human adipose tissue was introduced into *Xenopus laevis* oocytes by microinjection and the oocytes were incubated at 20° C. for 3 days in an isotonic culture medium (about 200 mOsm). The cultured oocytes were transferred to a hypotonic culture medium (about 40 mOsm). Photograph was taken 20 seconds and 40 seconds after transfer, and the sectional area and volume of each oocyte were determined using an image analyzer. The water permeability of the membrane protein was calculated as follows:

$$\text{Permeability (cm/sec)} = [(V_{40}-V_{20})/20]/[(A_{20} \times 10^{-2} \times 4) \times 1.384]$$

where $V_{20}$ denotes the oocyte volume ($cm^3$) after 20 seconds, $V_{40}$ denotes the oocyte volume ($cm^3$) after 40 seconds, and $A_{20}$ denotes the oocyte sectional area ($mm^2$) after 20 seconds.

The result is shown in Table 1. The water permeability found when purified water was used for microinjection in lieu of the RNA is also shown.

Further, the expression of the polypeptide of the present invention in said oocytes was confirmed by a C-terminal region immunoassay using the rabbit antiserum obtained by using the polypeptide of the present invention as synthesized in vitro.

TABLE 1

| | Water permeability (cm/sec) |
|---|---|
| Group in which RNA introduction was not made | $30.0 \times 10^{-4}$ |
| Group in which RNA introduction was made | $292.5 \times 10^{-4}$ |

As is evident from Table 1, the polypeptide encoded by the DNA sequence of the present invention caused an increase in water permeability after introduction into the oocytes. This result indicate that the polypeptide of the present invention has water channel activity.

INDUSTRIAL UTILIZABILITY

The present invention provides a novel protein having water channel activity and a novel DNA sequence encoding the protein. Said protein is one found in human adipose tissue for which the occurrence of water channels has not been reported as yet. The present invention makes it possible to develop novel therapies for water or fat metabolism-associated diseases in which said tissue is involved.

What is claimed is:

1. An isolated nucleotide molecule which encodes the polypeptide having water channel activity which has the amino acid sequence, shown in the sequence listing under SEQ ID NO:1.

2. An isolated nucleotide molecule having the sequence shown in the sequence listing under SEQ ID NO:2.

\* \* \* \* \*

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH:342 amino acids
      (B) TYPE: amino acid
      (D) TOPOLOGY: linear (ii) MOLECULE TYPE: peptide (xi) SEQUENCE DESCRIPTION: SEQ ID NO: 1:

```
Met Val Gln Ala Ser Gly His Arg Arg Ser Thr Arg Gly Ser Lys Met
                5                  10                  15

Val Ser Trp Ser Val Ile Ala Lys Ile Gln Glu Ile Leu Gln Arg Lys
                20                  25                  30

Met Val Arg Glu Phe Leu Ala Glu Phe Met Ser Thr Tyr Val Met Met
                35                  40                  45

Val Phe Gly Leu Gly Ser Val Ala His Met Val Leu Asn Lys Lys Tyr
            50                  55                  60

Gly Ser Tyr Leu Gly Val Asn Leu Gly Phe Gly Phe Gly Val Thr Met
 65                 70                  75                  80

Gly Val His Val Ala Gly Arg Ile Ser Gly Ala His Met Asn Ala Ala
                85                  90                  95

Val Thr Phe Ala Asn Cys Ala Leu Gly Arg Val Pro Trp Arg Lys Phe
                100                 105                 110

Pro Val Tyr Val Leu Gly Gln Phe Leu Gly Ser Phe Leu Ala Ala Ala
                115                 120                 125

Thr Ile Tyr Ser Leu Phe Tyr Thr Ala Ile Leu His Phe Ser Gly Gly
                130                 135                 140

Gln Leu Met Val Thr Gly Pro Val Ala Thr Ala Gly Ile Phe Ala Thr
145                 150                 155                 160

Tyr Leu Pro Asp His Met Thr Leu Trp Arg Gly Phe Leu Asn Glu Ala
                165                 170                 175

Trp Leu Thr Gly Met Leu Gln Leu Cys Leu Phe Ala Thr Thr Asp Gln
                180                 185                 190

Glu Asn Asn Pro Ala Leu Pro Gly Thr Glu Ala Leu Val Ile Gly Ile
                195                 200                 205

Leu Val Val Ile Ile Gly Val Ser Leu Gly Met Asn Thr Gly Tyr Ala
210                 215                 220

Ile Asn Pro Ser Arg Asp Leu Pro Pro Arg Ile Phe Thr Phe Ile Ala
225                 230                 235                 240

Gly Trp Gly Lys Gln Val Phe Ser Asn Gly Glu Asn Trp Trp Trp Val
                245                 250                 255

Pro Val Val Ala Pro Leu Leu Gly Ala Tyr Leu Gly Gly Ile Ile Tyr
                260                 265                 270

Leu Val Phe Ile Gly Ser Thr Ile Pro Arg Glu Pro Leu Lys Leu Glu
                275                 280                 285

Asp Ser Val Ala Tyr Glu Asp His Gly Ile Thr Val Leu Pro Lys Met
                290                 295                 300

Gly Ser His Glu Pro Thr Ile Ser Pro Leu Thr Pro Val Ser Val Ser
305                 310                 315                 320

Pro Ala Asn Arg Ser Ser Val His Pro Ala Pro Pro Leu His Glu Ser
                325                 330                 335

Met Ala Leu Glu His Phe
                340
```

(2) INFORMATION FOR SEQ ID NO:2:

(i) SEQUENCE CHARACTERISTICS:
        (A) LENGTH:1258 base pairs
        (B) TYPE: nucleic acid
        (C) STRANDEDNESS: double
        (D) TOPOLOGY: linear (ii) MOLECULE TYPE: cDNA to mRNA -continued

```
    (vi) ORIGINAL SOURCE:
         (A) ORGANISM: Homo sapiens
         (B) TISSUE TYPE: fat tissue (ix) FEATURE:
         (A) NAME/KEY: exon
         (B) LOCATION: F173..1198
         (C) IDENTIFICATION METHOD: by experiment
         (C) IDENTIFICATION METHOD: by experiment (xi) SEQUENCE DESCRIPTION: SEQ ID NO: 2:

GGCTCTGGAC TGGGGACACA GGGATAGCTG AGCCCCAGCT GGGGGTGGAA GCTGAGCCAG     60

GGACAGTCAC GGAGGAACAA GATCAAGATG CGCTGTAACT GAGAAGCCCC CAAGGCGGAG    120

GCTGAGAATC AGAGACATTT CAGCAGACAT CTACAAATCT GAAAGACAAA AC ATG GTT    178
                                                            Met Val
                                                             1

CAA GCA TCC GGG CAC AGG CGG TCC ACC CGT GGC TCC AAA ATG GTC TCC      226
Gln Ala Ser Gly His Arg Arg Ser Thr Arg Gly Ser Lys Met Val Ser
         5              10              15

TGG TCC GTG ATA GCA AAG ATC CAG GAA ATA CTG CAG AGG AAG ATG GTG      274
Trp Ser Val Ile Ala Lys Ile Gln Glu Ile Leu Gln Arg Lys Met Val
     20              25              30

CGA GAG TTC CTG GCC GAG TTC ATG AGC ACA TAT GTC ATG ATG GTA TTC      322
Arg Glu Phe Leu Ala Glu Phe Met Ser Thr Tyr Val Met Met Val Phe
 35              40              45              50

GGC CTT GGT TCC GTG GCC CAT ATG GTT CTA AAT AAA AAA TAT GGG AGC      370
Gly Leu Gly Ser Val Ala His Met Val Leu Asn Lys Lys Tyr Gly Ser
             55              60              65

TAC CTT GGT GTC AAC TTG GGT TTT GGC TTC GGA GTC ACC ATG GGA GTG      418
Tyr Leu Gly Val Asn Leu Gly Phe Gly Phe Gly Val Thr Met Gly Val
         70              75              80

CAC GTG GCA GGC CGC ATC TCT GGA GCC CAC ATG AAC GCA GCT GTG ACC      466
His Val Ala Gly Arg Ile Ser Gly Ala His Met Asn Ala Ala Val Thr
     85              90              95

TTT GCT AAC TGT GCG CTG GGC CGC GTG CCC TGG AGG AAG TTT CCG GTC      514
Phe Ala Asn Cys Ala Leu Gly Arg Val Pro Trp Arg Lys Phe Pro Val
 100             105             110

TAT GTG CTG GGG CAG TTC CTG GGC TCC TTC CTG GCG GCT GCC ACC ATC      562
Tyr Val Leu Gly Gln Phe Leu Gly Ser Phe Leu Ala Ala Ala Thr Ile
115             120             125             130

TAC AGT CTC TTC TAC ACG GCC ATT CTC CAC TTT TCG GGT GGA CAG CTG      610
Tyr Ser Leu Phe Tyr Thr Ala Ile Leu His Phe Ser Gly Gly Gln Leu
             135             140             145

ATG GTG ACC GGT CCC GTC GCT ACA GCT GGC ATT TTT GCC ACC TAC CTT      658
Met Val Thr Gly Pro Val Ala Thr Ala Gly Ile Phe Ala Thr Tyr Leu
         150             155             160

CCT GAT CAC ATG ACA TTG TGG CGG GGC TTC CTG AAT GAG GCG TGG CTG      706
Pro Asp His Met Thr Leu Trp Arg Gly Phe Leu Asn Glu Ala Trp Leu
     165             170             175

ACC GGG ATG CTC CAG CTG TGT CTC TTC GCC ATC ACG GAC CAG GAG AAC      754
Thr Gly Met Leu Gln Leu Cys Leu Phe Ala Ile Thr Asp Gln Glu Asn
 180             185             190

AAC CCA GCA CTG CCA GGA ACA GAG GCG CTG GTG ATA GGC ATC CTC GTG      802
Asn Pro Ala Leu Pro Gly Thr Glu Ala Leu Val Ile Gly Ile Leu Val
195             200             205             210

GTC ATC ATC GGG GTG TCC CTT GGC ATG AAC ACA GGA TAT GCC ATC AAC      850
Val Ile Ile Gly Val Ser Leu Gly Met Asn Thr Gly Tyr Ala Ile Asn
             215             220             225

CCG TCC CGG GAC CTG CCC CCC CGC ATC TTC ACC TTC ATT GCT GGT TGG      898
Pro Ser Arg Asp Leu Pro Pro Arg Ile Phe Thr Phe Ile Ala Gly Trp
         230             235             240
```

```
GGC AAA CAG GTC TTC AGC AAT GGG GAG AAC TGG TGG TGG GTG CCA GTG        946
Gly Lys Gln Val Phe Ser Asn Gly Glu Asn Trp Trp Trp Val Pro Val
        245                 250                 255

GTG GCA CCA CTT CTG GGT GCC TAT CTA GGT GGC ATC ATC TAC CTG GTC        994
Val Ala Pro Leu Leu Gly Ala Tyr Leu Gly Gly Ile Ile Tyr Leu Val
        260                 265                 270

TTC ATT GGC TCC ACC ATC CCA CGG GAG CCC CTG AAA TTG GAG GAT TCT       1042
Phe Ile Gly Ser Thr Ile Pro Arg Glu Pro Leu Lys Leu Glu Asp Ser
275                 280                 285                 290

GTG GCG TAT GAA GAC CAC GGG ATA ACC GTA TTG CCC AAG ATG GGA TCT       1090
Val Ala Tyr Glu Asp His Gly Ile Thr Val Leu Pro Lys Met Gly Ser
                295                 300                 305

CAT GAA CCC ACG ATC TCT CCC CTC ACC CCC GTC TCT GTG AGC CCT GCC       1138
His Glu Pro Thr Ile Ser Pro Leu Thr Pro Val Ser Val Ser Pro Ala
            310                 315                 320

AAC AGA TCT TCA GTC CAC CCT GCC CCA CCC TTA CAT GAA TCC ATG GCC       1186
Asn Arg Ser Ser Val His Pro Ala Pro Pro Leu His Glu Ser Met Ala
        325                 330                 335

CTA GAG CAC TTC TAAGCAGAGA TTATTTGTGA TCCCATCCAT TCCCCAATAA           1238
Leu Glu His Phe
    340

AGCAAGGCTT GTCCGACAAA                                                 1258
```